(12) United States Patent
Hayashida

(10) Patent No.: US 10,245,003 B2
(45) Date of Patent: Apr. 2, 2019

(54) RADIATION IMAGING APPARATUS, RADIATION IMAGING SYSTEM, RADIATION DETECTION APPARATUS, IMAGING CONTROL APPARATUS, IMAGING CONTROL METHOD, AND STORAGE MEDIUM

(71) Applicant: CANON KABUSHIKI KAISHA, Tokyo (JP)

(72) Inventor: Shinsuke Hayashida, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 504 days.

(21) Appl. No.: 14/972,328

(22) Filed: Dec. 17, 2015

(65) Prior Publication Data

US 2016/0183908 A1 Jun. 30, 2016

(30) Foreign Application Priority Data

Dec. 24, 2014 (JP) .................. 2014-261246

(51) Int. Cl.
*H05G 1/64* (2006.01)
*G01D 18/00* (2006.01)
(Continued)

(52) U.S. Cl.
CPC ............ *A61B 6/585* (2013.01); *A61B 6/4291* (2013.01); *A61B 6/542* (2013.01); *G01T 1/02* (2013.01)

(58) Field of Classification Search
CPC . G06T 2207/10116; G06T 2207/30004; G06T 5/009; G06T 5/007; G06T 5/50; A61B 6/585; A61B 6/0407; A61B 6/4405; A61B 6/4441; A61B 6/4464; A61B 6/5211; A61B 6/5258; A61B 5/055; A61B 5/4836; A61B 6/4291; A61B 6/542; A61B 6/06; A61B 6/463; A61B 6/504; A61B 6/52; A61B 6/5235; A61B 6/545; A61B 6/00; A61B 6/5252; H04N 5/32; H04N 5/243; H04N 5/367; H04N 5/235; H04N 5/2355;
(Continued)

(56) References Cited

U.S. PATENT DOCUMENTS 7,227,154 B2 * 6/2007 Hoernig ................ G01T 1/1641
250/395
7,729,527 B2 * 6/2010 Maschauer ............... G06T 5/50
378/98.7
(Continued)

FOREIGN PATENT DOCUMENTS

JP 2002-045354 2/2002
JP 2002-236907 8/2002
(Continued)

*Primary Examiner* — Irakli Kiknadze
(74) *Attorney, Agent, or Firm* — Venable LLP

(57) ABSTRACT

A radiation imaging apparatus includes: a radiation detection unit including an image obtaining pixel for obtaining a radiation image and a dose obtaining pixel for obtaining a radiation dose; a generating unit configured to generate calibration data for calibrating an output value of the dose obtaining pixel by comparing an output value of the image obtaining pixel and the output value of the dose obtaining pixel; and a calibration unit configured to calibrate the output value of the dose obtaining pixel by using the calibration data.

18 Claims, 10 Drawing Sheets

(51) Int. Cl.
*G01N 23/04* (2018.01)
*A61B 6/00* (2006.01)
*G01T 1/02* (2006.01)

(58) Field of Classification Search
CPC ......... H04N 5/325; G01T 1/02; G01T 1/1641; G01T 1/2914
USPC ...................... 378/4, 19, 98.9, 209, 62, 98.7
See application file for complete search history.

(56) References Cited

U.S. PATENT DOCUMENTS

| | | | |
|---|---|---|---|
| 9,014,461 B2 | 4/2015 | Hayashida | G06T 7/0012 |
| 2002/0025022 A1 | 2/2002 | Kaifu et al. | 378/97 |
| 2004/0096035 A1 | 5/2004 | Yamazaki et al. | 378/97 |
| 2012/0020541 A1 | 1/2012 | Hayashida | 382/132 |
| 2012/0305791 A1* | 12/2012 | Watanabe | G01T 1/247 |
| | | | 250/394 |
| 2014/0050301 A1* | 2/2014 | Liu | G06T 5/009 |
| | | | 378/62 |
| 2014/0341350 A1* | 11/2014 | Muroi | A61B 6/463 |
| | | | 378/62 |

FOREIGN PATENT DOCUMENTS

| | | |
|---|---|---|
| JP | 2004-166724 | 6/2004 |
| JP | 2011-250810 | 12/2011 |
| JP | 2014-045938 | 3/2014 |

* cited by examiner

☐ IMAGE OBTAINING PIXEL
■ DOSE OBTAINING PIXEL

PLAN VIEW (WITH GRID)

☐ IMAGE OBTAINING PIXEL
■ DOSE OBTAINING PIXEL

PLAN VIEW (WITHOUT GRID)

☐ IMAGE OBTAINING PIXEL
■ DOSE OBTAINING PIXEL

SECTIONAL VIEW (WITH GRID)

☐ IMAGE OBTAINING PIXEL
■ DOSE OBTAINING PIXEL

SECTIONAL VIEW (WITHOUT GRID)

FIG. 5E

| 10 | 5 | 10 | 10 | 9 |
|---|---|---|---|---|
| 10 | 5 | 10 | 10 | 9 |
| 10 | 5 | — DOSE OBTAINING PIXEL | 10 | 9 |
| 10 | 5 | 10 | 10 | 9 |
| 10 | 5 | 10 | 10 | 9 |

OUTPUT EXAMPLE OF EACH PIXEL (WITH GRID)

FIG. 5F

| 10 | 10 | 10 | 10 | 10 |
|---|---|---|---|---|
| 10 | 10 | 10 | 10 | 10 |
| 10 | 10 | — DOSE OBTAINING PIXEL | 10 | 10 |
| 10 | 10 | 10 | 10 | 10 |
| 10 | 10 | 10 | 10 | 10 |

OUTPUT EXAMPLE OF EACH PIXEL (WITHOUT GRID)

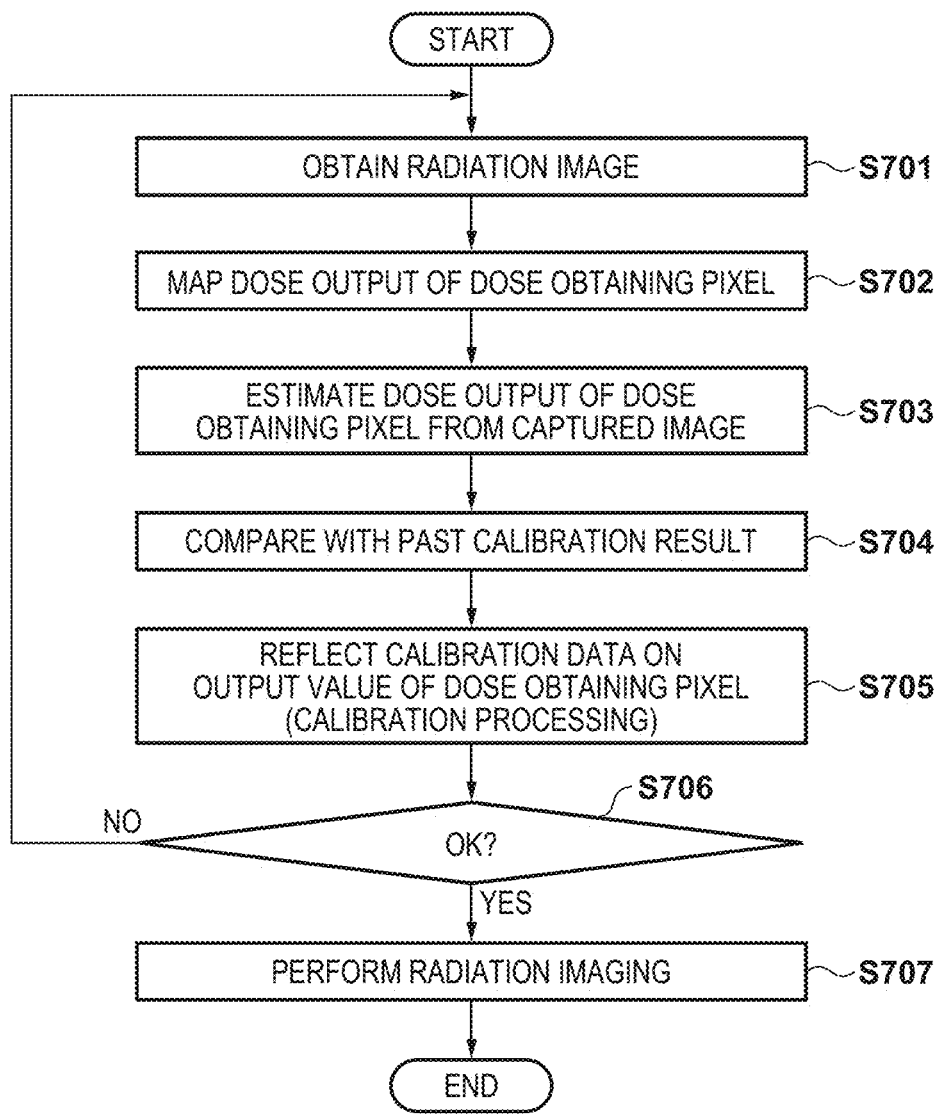

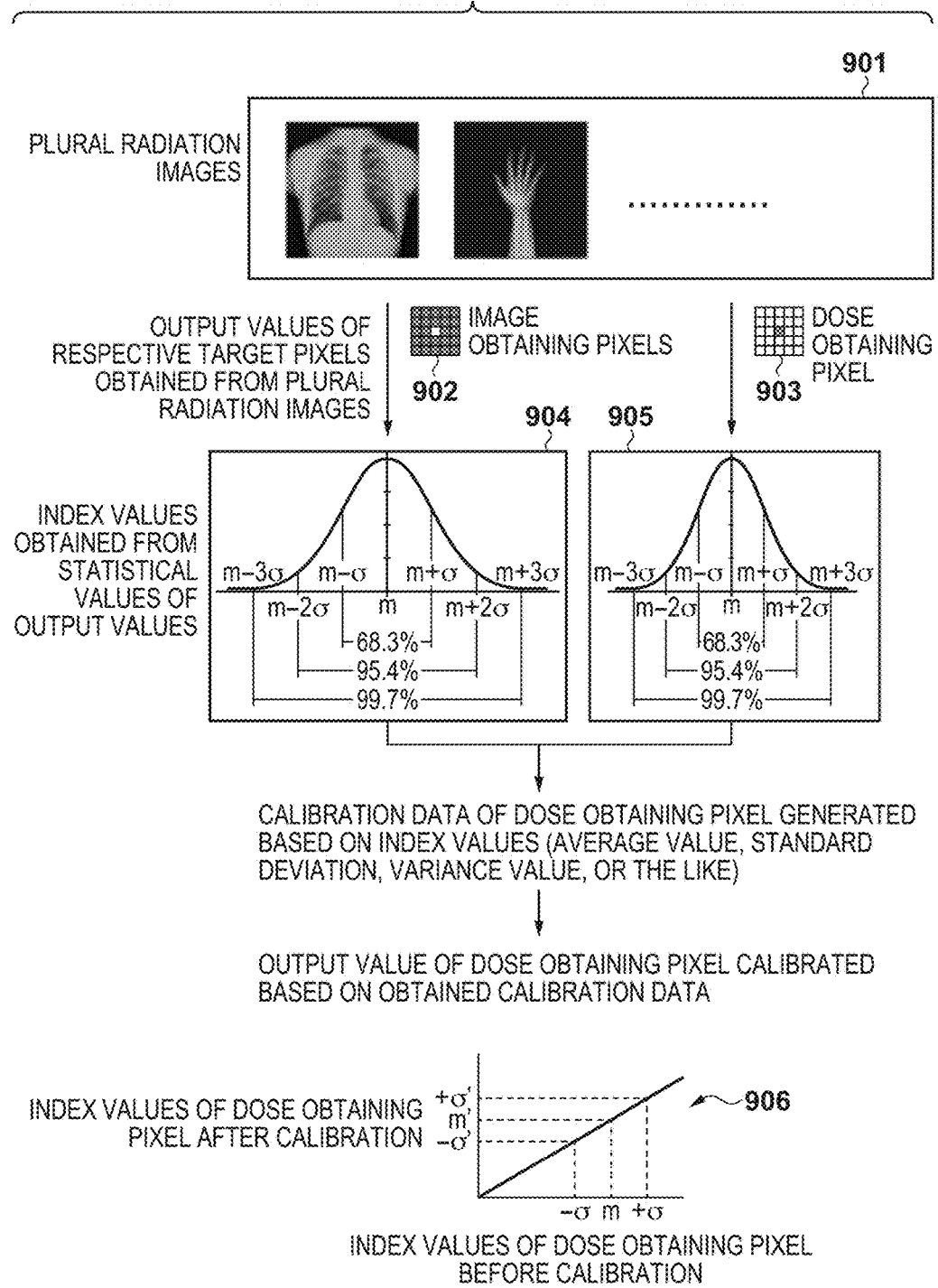

RADIATION IMAGING APPARATUS, RADIATION IMAGING SYSTEM, RADIATION DETECTION APPARATUS, IMAGING CONTROL APPARATUS, IMAGING CONTROL METHOD, AND STORAGE MEDIUM

BACKGROUND OF THE INVENTION

Field of the Invention

The present invention relates to a radiation imaging apparatus, a radiation imaging system, a radiation detection apparatus, an imaging control apparatus, an imaging control method, and a storage medium.

Description of the Related Art

In recent years, a digital radiation imaging apparatus that performs imaging by an imaging unit which uses a photoelectric conversion element has become popular in radiation imaging for medical diagnostic purposes. Since a radiation fluoroscopic image can be obtained without having to develop a film or the like, the digital radiation imaging apparatus has immediacy and is superior in terms of its ability to perform image processing and the like.

In the digital radiation imaging apparatus, there is also provided an automatic exposure control (AEC) unit that includes an AEC detector for the purpose of minimizing radiation exposure to the human body in addition to appropriately irradiating an object with a radiation dose necessary for the imaging apparatus. The automatic exposure control unit is sometimes referred to as a phototimer. Japanese Patent Laid-Open No. 2002-45354 discloses a technique for grasping and controlling the radiation dose by nondestructively reading out the radiation that enters the photoelectric conversion element without using a phototimer. Japanese Patent Laid-Open No. 2004-166724 discloses a technique for calibrating the output of a dose grasping photoelectric conversion element in accordance with a grid.

In a conventional apparatus, a dose grasping pixel has a different usage history compared to an image capturing pixel and requires a higher frequency of output value calibration than the image capturing pixel in terms of the influence of temporal change in cases of long term use, installation of the radiation imaging apparatus, and periodic maintenance. If the frequency of calibration is to be higher, an output value calibration of the dose grasping pixel that can be performed more simply from a user perspective is required.

In addition, when a scattering radiation removing grid is to be used, the characteristics of the output signals output from the pixels differ depending on the relative positional relationship between the grid pitch and the pixel pitch. Therefore, in the conventional apparatus arrangement, it is difficult to simply calibrate, by using the output signal, the output value of the dose grasping pixel in accordance with the state of usage of the radiation imaging apparatus.

The present invention provides, in consideration of the above problem, a radiation imaging technique capable of calibrating a dose grasping pixel by using the respective output values of the dose grasping pixel and image obtaining pixels in accordance with the state of usage of the radiation imaging apparatus.

SUMMARY OF THE INVENTION

According to one aspect of the present invention, there is provided a radiation imaging apparatus comprising: a radiation detection unit including an image obtaining pixel for obtaining a radiation image and a dose obtaining pixel for obtaining a radiation dose; a generating unit configured to generate calibration data for calibrating an output value of the dose obtaining pixel by comparing an output value of the image obtaining pixel and the output value of the dose obtaining pixel; and a calibration unit configured to calibrate the output value of the dose obtaining pixel by using the calibration data.

According to another aspect of the present invention, there is provided a radiation imaging system comprising: a radiation generating unit configured to generate radiation; a radiation detection unit including an image obtaining pixel for obtaining a radiation image based on the radiation and a dose obtaining pixel for obtaining a radiation dose; a generating unit configured to generate calibration data for calibrating an output value of the dose obtaining pixel by comparing an output value of the image obtaining pixel and the output value of the dose obtaining pixel; and a calibration unit configured to calibrate the output value of the dose obtaining pixel by using the calibration data.

According to still another aspect of the present invention, there is provided an imaging control apparatus that controls a radiation detection unit including an image obtaining pixel for obtaining a radiation image and a dose obtaining pixel for obtaining a radiation dose, comprising: a generating unit configured to generate calibration data for calibrating an output value of the dose obtaining pixel by comparing an output value of the image obtaining pixel and the output value of the dose obtaining pixel; and a calibration unit configured to calibrate the output value of the dose obtaining pixel by using the calibration data.

According to yet another aspect of the present invention, there is provided an imaging control method of a radiation imaging apparatus comprising: detecting radiation by using a radiation detection unit including an image obtaining pixel for obtaining a radiation image and a dose obtaining pixel for obtaining a radiation dose; generating calibration data for calibrating an output value of the dose obtaining pixel by comparing an output value of the image obtaining pixel and the output value of the dose obtaining pixel; and calibrating the output value of the dose obtaining pixel by using the calibration data.

Further features of the present invention will become apparent from the following description of exemplary embodiments (with reference to the attached drawings).

BRIEF DESCRIPTION OF THE DRAWINGS

FIGS. 5A to 5F are views for explaining the arrangement of the radiation imaging apparatus according to the second embodiment;

FIG. 7 is a flowchart for explaining the operation sequence of a radiation imaging apparatus according to the fourth embodiment;

FIG. 9 is a view showing a detailed example of calibration data generating processing according to an embodiment.

DESCRIPTION OF THE EMBODIMENTS

Embodiments of the present invention will be exemplarily described in detail below with reference to the accompanying drawings. Note that components to be described in these embodiments are merely examples. The technical scope of the present invention is defined by the scope of the claims, and is not limited by the following embodiments.

(First Embodiment)

Figure 1:
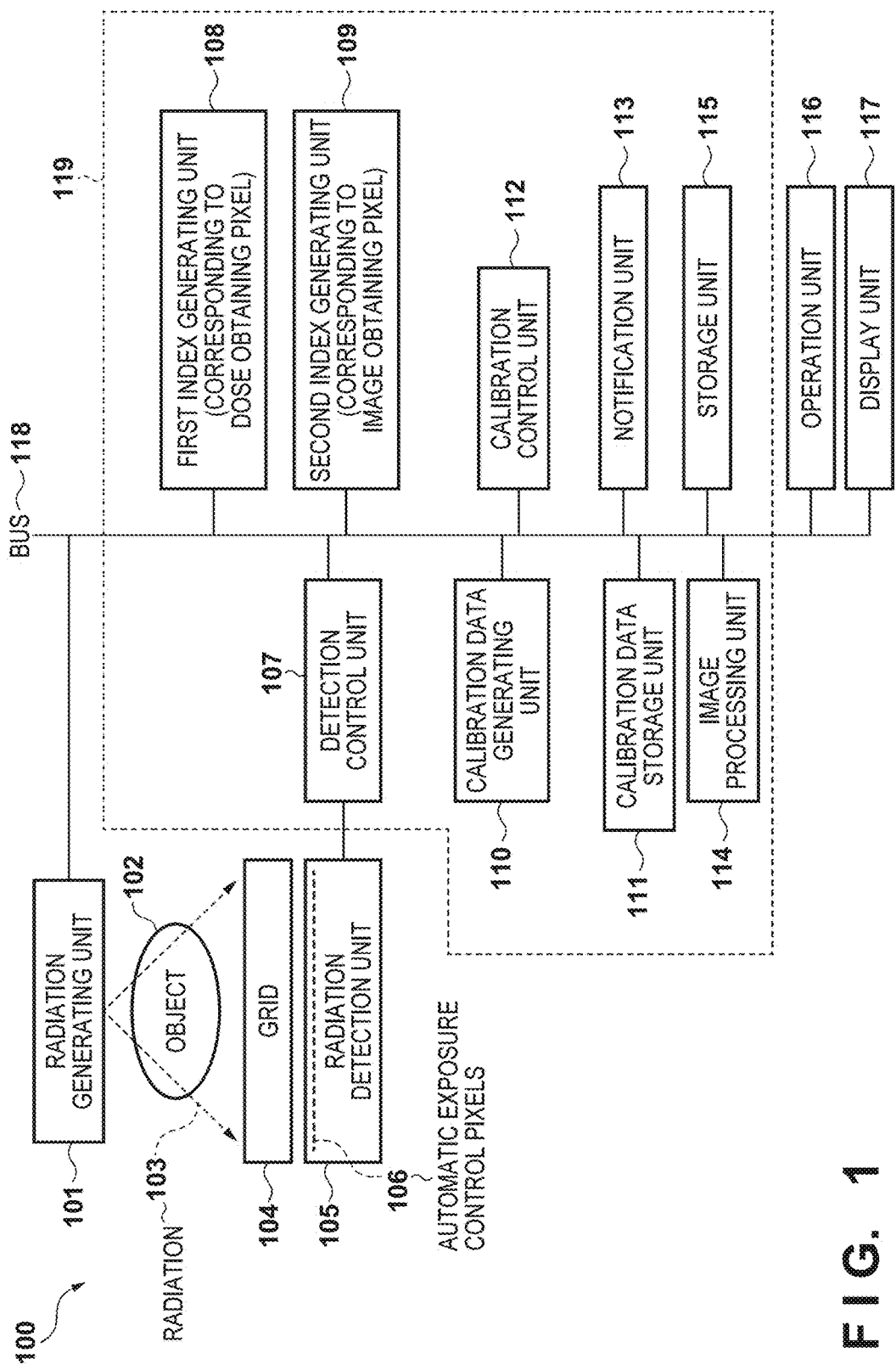
FIG. 1 is a block diagram for explaining the arrangement of a radiation imaging apparatus according to the first embodiment.

FIG. 1 is a block diagram showing the schematic arrangement of a radiation imaging apparatus 100 (radiation imaging system) according to the first embodiment. In FIG. 1, a radiation generating unit 101 generates radiation. Reference numeral 102 denotes an object. A radiation detection unit 105 (radiation detection apparatus) is a detection unit that detects radiation. Radiation 103 (X-rays) generated in the radiation generating unit 101 is detected by the radiation detection unit 105 via a scattering radiation removing grid 104 (to be simply referred to as a grid, hereinafter). The radiation detection unit 105 (two-dimensional radiation sensor) includes radiation image capturing pixels (image obtaining pixels) and automatic exposure control (AEC) pixels 106 (dose obtaining pixels). The radiation detection unit 105 can be formed as a two-dimensional radiation sensor in which the image obtaining pixels and the dose obtaining pixels are arranged two-dimensionally. In this two-dimensional pixel arrangement, more than one image obtaining pixel is arranged around each dose obtaining pixel. The radiation imaging apparatus 100 can execute automatic exposure control based on an output signal of each automatic exposure control pixel 106 (dose obtaining pixel).

A detection control unit 107 supplies a driving signal for controlling the radiation detection unit 105. The detection control unit 107 can determine whether the radiation detection unit 105 is operating normally by monitoring a response signal of the radiation detection unit 105 to the driving signal of the detection control unit 107.

A first index generating unit 108 generates index values (index information) from the output value (output signal) of the automatic exposure control pixel 106 (dose obtaining pixel). A second index generating unit 109 generates index values (index information) from output values of the image obtaining pixels. The index values (index information) include information obtained from a statistical value based on a result by statistically processing each output value, for example, the average value, the standard deviation, and the variance value as normal distribution information.

A calibration data generating unit 110 generates calibration data based on a comparison of the index values (index information) generated by the first index generating unit 108 and the index values (index information) generated by the second index generating unit 109. In the first embodiment, calibration data is generated based on the index values (index information) generated from the output signal of the dose obtaining pixel and index information generated from the output signals of the radiation image capturing pixels (image obtaining pixels) other than the dose obtaining pixel. Generation of calibration data will be described in detail later.

A calibration data storage unit 111 stores the calibration data generated in the calibration data generating unit 110. A calibration control unit 112 calibrates the output value (output signal) of the automatic exposure control pixel 106 (image obtaining pixel) based on the calibration data stored in the calibration data storage unit 111. A notification unit 113 causes a display unit 117 to display a warning to notify a user of the calibration result.

An image processing unit 114 generates a radiation image based on the output values (output signals) output from the radiation image capturing pixels (image obtaining pixels). An operation unit 116 functions as a user interface for operating the radiation imaging apparatus 100. The display unit 117 displays the radiation image, the calibration result of the automatic exposure control pixel, the warning, or the like. A storage unit 115 stores various settings of the radiation imaging apparatus 100 and the radiation images. A bus 118 joins each unit that forms the radiation imaging apparatus 100. Each unit of the radiation imaging apparatus 100 can transmit/receive data via the bus 118.

In the arrangement of FIG. 1, the units which are shown within broken lines 119 function as an imaging control apparatus that controls the radiation detection unit 105.

(Operation Sequence of Radiation Imaging Apparatus)

Figure 2:
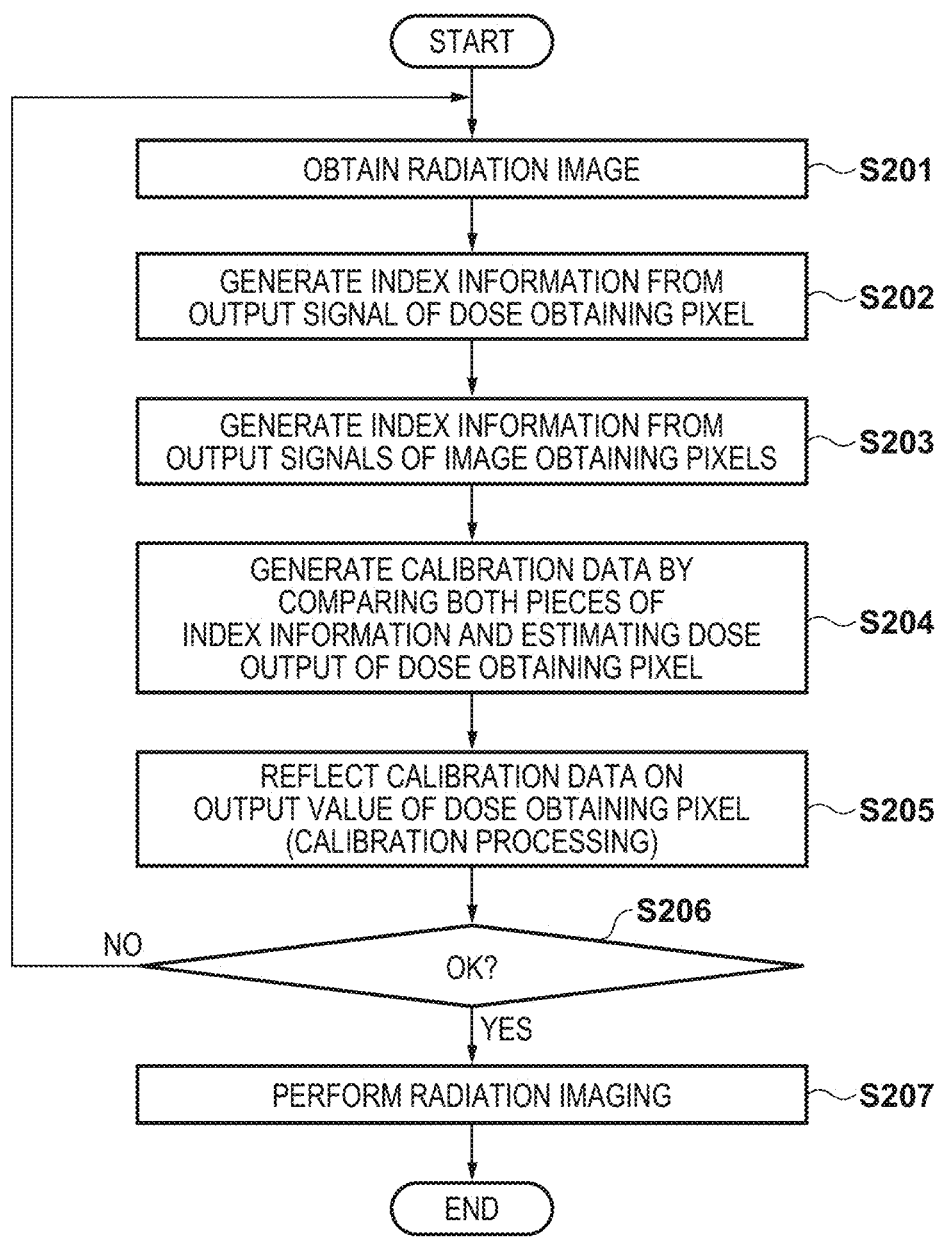
FIG. 2 is a flowchart for explaining the operation sequence of the radiation imaging apparatus according to the first embodiment.

FIG. 2 is a flowchart for explaining the operation sequence of the radiation imaging apparatus according to the first embodiment. In step S201, the radiation detection unit 105 obtains a radiation image. The radiation 103 from the radiation generating unit 101 reaches the radiation detection unit 105, and an output signal is output from the automatic exposure control pixel 106 (dose obtaining pixel) when the radiation image is obtained by the radiation detection unit 105. This radiation image can be obtained from a test image (calibration image) capturing operation performed by a serviceman or the like before or at the time of installing the radiation imaging apparatus or from capturing a captured image with an object.

In step S202, when the radiation image is captured in the preceding step S201, the first index generating unit 108 generates the index information from the output signal of the automatic exposure control pixel 106 (dose obtaining pixel). The calibration data storage unit 111 stores the output signal output from the automatic exposure control pixel 106 (dose obtaining pixel) and the index information generated by the first index generating unit 108.

Also, in step S203, the second index generating unit 109 generates index information from the output signals of the image obtaining pixels. The image obtaining pixels are the plurality of pixels arranged around the automatic exposure control pixel 106 (dose obtaining pixel). The calibration data storage unit 111 stores the output signals output from the image obtaining pixels and the index information generated by the second index generating unit 109.

In step S204, the calibration data generating unit 110 compares the index information (first index information) generated by the first index generating unit 108 and the index information (second index information) generated by the second index generating unit 109 that were obtained in steps S202 and S203, respectively. Based on the comparison result, the calibration data generating unit 110 estimates the dose output of the dose obtaining pixel, generates calibration data so that the dose output of the dose obtaining pixel becomes equal to the outputs of the image obtaining pixels, and stores the generated calibration data in the calibration data storage unit 111. For example, the calibration data generating unit 110 compares the index information based on the output value of the dose obtaining pixel and the index information based on the output values of the plurality of pixels (image obtaining pixels) arranged around the dose obtaining pixel. If the index information based on the output value of the dose obtaining pixel is smaller than the index information based on the output values of the image obtaining pixels, the calibration data generating unit 110 generates the calibration data for calibrating the output value of the dose obtaining pixel so that the two types of index information will become equal. Based on the calibration data, the output value of the dose obtaining pixel is calibrated and reflected on the subsequent and later radiation imaging operations. Note that although this processing has described the processing for generating calibration data based on an index information comparison result, the scope of the present invention is not limited to this example. For example, the calibration data generating unit 110 can generate the calibration data for calibrating the output value of the dose obtaining pixel by comparing the output value of the dose obtaining pixel and the output values of the image obtaining pixels.

In step S205, the calibration control unit 112 reflects the calibration data generated by the calibration data generating unit 110 on the output value of the automatic exposure control pixel 106 (dose obtaining pixel) and calibrates the output value of the dose obtaining pixel (calibration processing). The calibration data generated in step S204 and the calibration result of the output value (output signal) of the automatic exposure control pixel 106 (dose obtaining pixel) in step S205 are displayed on the display unit 117.

Typically, quantization noise is often included in the radiation generated from the radiation generating unit 101, and the radiation dose to be input can vary. It is preferable to capture a plurality of images in order to reduce this variation of the radiation dose. If the imaging count is less than the reference count (for example, 4 to 16 images) (NO in step S206), the process returns to step S201 for radiation image obtainment, and the processing is repeated in the same manner.

If the imaging count has reached the reference count (YES in step S206), the process advances to step S207. Note that the determination in step S206 is not limited to comparing the imaging count and the reference count. For example, if the user determines that the variation of the output value has been eliminated based on the calibration result displayed on the display unit 117, the process can advance to step S207 based on the determination of the user.

In the radiation imaging operation of step S207, the automatic exposure control pixel 106 (dose obtaining pixel) performs real-time detection under the control of the detection control unit 107 and outputs the calibrated correct output value (output signal) to the detection unit 107. The detection control unit 107 accumulates the output value (output signal). If the accumulated value of the calibrated output value (output signal) is larger than a predetermined threshold which indicates that a predetermined radiation dose has been reached, the detection control unit 107 outputs a radiation exposure termination signal to the radiation generating unit 101. The radiation generating unit 101 stops generating the radiation upon receiving the radiation exposure termination signal.

Note that the user can select whether to use, for the subsequent radiation imaging operation, the calibration result of the automatic exposure control pixel 106 (dose obtaining pixel) of the preceding image that was captured earlier. For example, if the calibration result of the dose obtaining pixel of the preceding captured image cannot be used due to differences in imaging conditions or the like, the user can select not to use the previous calibration result by operation input via a GUI displayed on the screen of the display unit 117.

Furthermore, the preceding image can be not only one image but also a plurality of images, as a matter of course. In a case in which a plurality of images are to be used, the automatic exposure control pixel 106 (dose obtaining pixel) can output a calibrated signal based on a calibration result obtained by increasing the weighting (increasing the weighting coefficient) of the immediately preceding image.

(Arrangement of Radiation Imaging Apparatus)

Figure 3A:
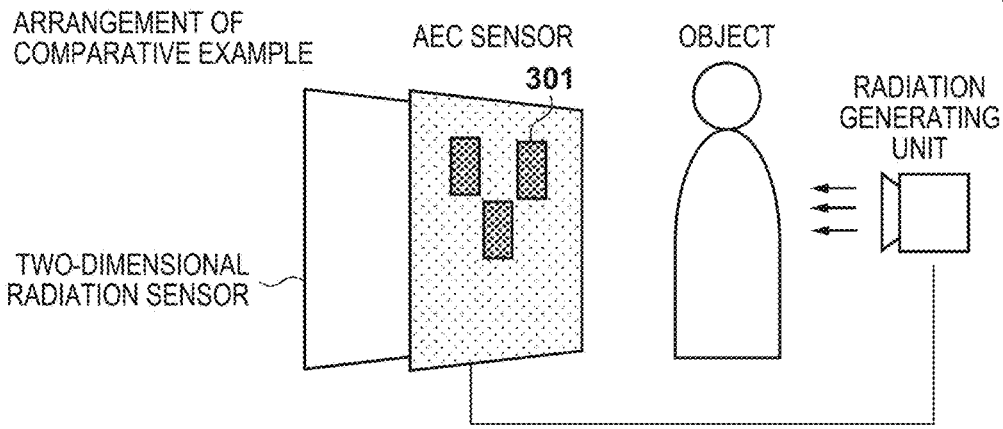
FIGS. 3A and 3B are views for explaining the arrangement of a comparative example and a view for explaining the arrangement of the radiation imaging apparatus according to the first embodiment, respectively.
Figure 3B:
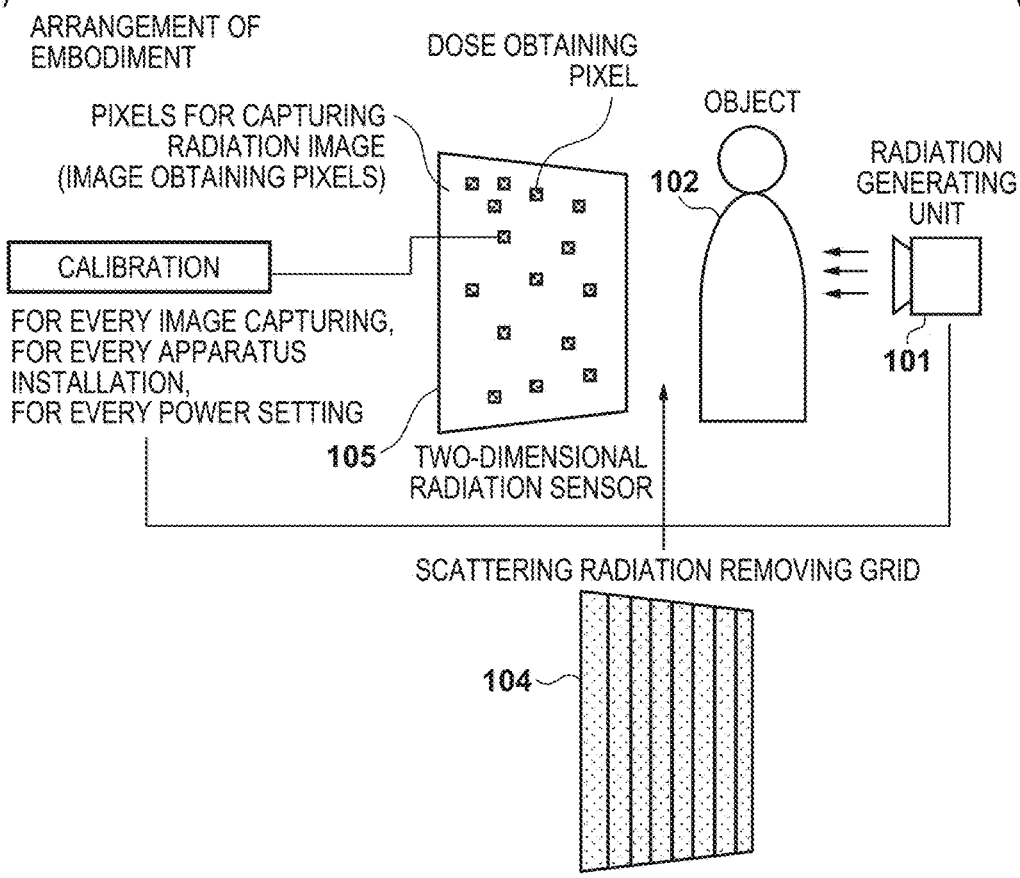

FIGS. 3A and 3B are views for explaining the arrangement of the radiation imaging apparatus. FIG. 3A shows the arrangement of a comparative example, and FIG. 3B shows the arrangement of the radiation imaging apparatus of the first embodiment. In the arrangement of the comparative example (FIG. 3A), the radiation from the radiation generating unit is transmitted through the object and reaches an AEC sensor. When the radiation dose that reaches each predetermined sensor area 301 in the AEC sensor becomes larger than a preset threshold, the AEC sensor outputs a signal to the radiation generating unit to stop irradiating the object with radiation.

In the arrangement of the first embodiment (FIG. 3B), the radiation from the radiation generating unit 101 is transmitted through the object 102 and directly reaches the radiation detection unit 105 (two-dimensional radiation sensor) for capturing an image. The radiation imaging apparatus can execute automatic exposure control (AEC) based on the output signal of each automatic exposure control pixel 106 (dose obtaining pixel) without using the AEC sensor shown in the comparative example. The radiation image capturing pixels (image obtaining pixels) and each corresponding automatic exposure control pixel 106 (dose obtaining pixel) are included in the pixel array of the radiation detection unit 105 (two-dimensional radiation sensor). Each automatic exposure control pixel 106 (dose obtaining pixel) detects the arrival amount of radiation and outputs an arrival radiation dose at a time before the end of image capturing. In this point, the automatic exposure control pixel 106 (dose obtaining pixel) differs from the image obtaining pixels in the output characteristics of the absolute value of pixel values. When the automatic exposure pixel 106 (dose obtaining pixels) is used for capturing a radiation image, the distribution of pixel values may become non-uniform due to the differences in output characteristics. For example, if the arrangement number of the automatic exposure control pixels 106 (dose obtaining pixels) is increased or a plurality of automatic exposure control pixels 106 (dose obtaining pixels) are arranged to be next to each other, a defective region may be generated in the image region. Therefore, as long as the objectives of grasping the radiation dose at an early stage and grasping the dose for necessary irradiation regions are not lost, it is better to have a smaller number of automatic exposure control pixels. Assume that the radiation detection unit 105 is formed by setting the minimum necessary arrangement number of automatic exposure control pixels 106 (dose obtaining pixels) so that the radiation dose can be grasped at an early stage and the dose in each necessary irradiation region can be grasped.

On the other hand, if the arrangement number of automatic exposure control pixels 106 (dose obtaining pixels) is small, the detection precision may vary due to the influence of the quantization noise included in the radiation generated by the radiation generating unit 101. The first embodiment tries to improve the detection precision of the radiation dose by using the output values of the radiation image capturing pixels (image obtaining pixels) which are arranged around each automatic exposure control pixel 106 (dose obtaining pixel) to calibrate the output value of the dose obtaining pixel. In order to improve this detection precision, calibration processing can be performed for each installed apparatus per each image. Particularly, variations in the detection precision can be effectively calibrated when the grid 104 is used. The detailed contents of the calibration method of each automatic exposure control pixel for a case in which the grid 104 is used will be described in the second embodiment.

(Detailed Example of Calibration Data Generation)

FIG. 9 is a view exemplarily showing processing for performing calibration of the automatic exposure control pixel 106 (dose obtaining pixel) by using a plurality of radiation images.

First, the calibration data generating unit 110 reads out a plurality of radiation images from the storage unit 115 (901). Next, the calibration data generating unit 110 obtains the output values of the image obtaining pixels as target pixels from the plurality of radiation images (902). The calibration data generating unit 110 obtains the output value of the dose obtaining pixel for each radiation imaging operation from each radiation image at the time of the image capturing operation (903). When the scattering radiation removing grid is used, the characteristic of the output signal output from each pixel varies in accordance with the relative positional relationship between the grid pitch and the pixel pitch. Therefore, in order to reduce the influence of the grid and calibrate the dose obtaining pixel, the calibration data generating unit 110 obtains, as the image obtaining pixels, the output values of a plurality of pixels in the vicinity of the dose obtaining pixel. The calibration data generating unit 110 uses, for example, the average value or the statistical value of the 25×25 pixels in the vicinity of the dose obtaining pixel to estimate the output result obtained when the dose obtaining pixel is a normal image obtaining pixel. In this case, the radiation image to be included as a target when obtaining the radiation images can be a calibration image without an object or a plurality of radiation images with an object. In the case of the calibration image without an object, the calibration data generating unit 110 performs processing by obtaining each output value of the dose obtaining pixel from a plurality of images for calibration so that the radiation quantization noise and the changes in the ambient environment will not appear.

The second index generating unit 109 statistically processes the output values of the image obtaining pixels that were applied to the plurality of radiation images and obtains the index values (index information) from the statistical values based on the result of the statistical processing (904). The first index generating unit 108 statistically processes the output value of the dose obtaining pixel and obtains index values (index information) from the statistical value based on the result of the statistical processing (905). The index values (index information) include, for example, as normal distribution information, the average value, the standard deviation, and the variance value. The calibration data generating unit 110 generates calibration data so that the average value, the standard deviation, and the variance value will match. When the output value of the dose obtaining pixel and the output values of the image obtaining pixels become equal by calibrating the dose obtaining pixel by using the generated calibration data, the calibration control unit 112 can cancel the noise or the like entering the radiation image.

The calibration data generating unit 110 compares the average value, the standard deviation, and the variance value as the index values (index information) of the 25×25 pixels (image obtaining pixels) in the vicinity of the dose obtaining pixel and the average value, the standard deviation, and the variance value of the index values (index information) of the dose obtaining pixel. The calibration data generating unit 110 generates a value which can nullify the difference between the both types of pixels as calibration data for calibrating the output value of each dose obtaining pixel, so that the index values (index information) of the image obtaining pixels and the index values (index information) of the dose obtaining pixel will match. The calibration data generating unit 110 stores the generated calibration data in the calibration data storage unit 111. The calibration control unit 112 obtains the calibration data from the calibration data storage unit 111 and calibrates the output value of the dose obtaining pixel. For example, a graph 906 of FIG. 9 is a graph showing the correspondence between the index values of the dose obtaining pixel before calibration and the index values of the dose obtaining pixel after calibration. The abscissa shows the index values of the dose obtaining pixel before calibration and the ordinate represents the index values of the dose obtaining pixel after calibration. In the graph 906 of FIG. 9, an average value m of the dose obtaining pixel before calibration is associated with an average value m' of the dose obtaining pixel after calibration. Standard deviations ±σ of the dose obtaining pixel before calibration are associated with standard deviations ±σ' of the dose obtaining pixel after calibration. By associating standard deviations such as ±2σ, ±3σ, and the like for before and after calibration in the same manner, a calibration table of the dose obtaining pixel can be created.

According to the first embodiment, calibration of the output value of each dose grasping pixel can be simply performed in accordance with the state of usage of the radiation imaging apparatus. Through the calibration of the output value of the dose grasping pixel, a precise incident radiation dose can be estimated to execute automatic exposure control. In addition, calibration of the output value of the dose obtaining pixel can be performed while capturing a radiation image and the throughput of the radiation imaging apparatus can be improved.

(Second Embodiment)

Figure 4:
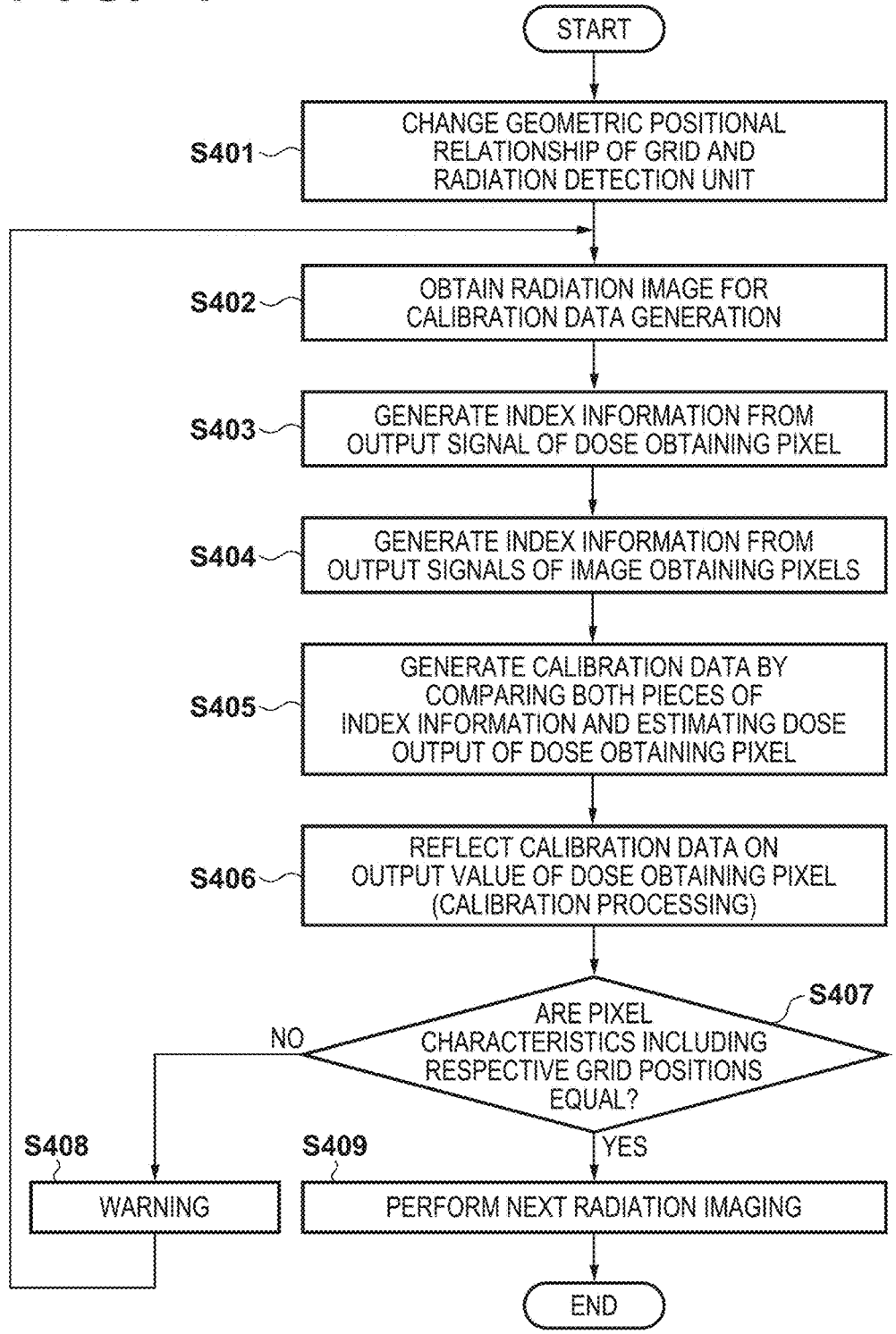
FIG. 4 is a flowchart for explaining the operation sequence of a radiation imaging apparatus according to the second embodiment.

A calibration method of each automatic exposure control pixel 106 when using a grid 104 will be described in the second embodiment. FIG. 4 is a flowchart for explaining the operation sequence of a radiation imaging apparatus according to the second embodiment, and FIGS. 5A to 5F are views for explaining the arrangement of the radiation imaging apparatus according to the second embodiment.

The grid 104 of FIG. 1 will be described first. The grid 104 is a plate member obtained by thinly cutting out a stack, made by alternately stacking lead plates and aluminum plates, in a direction perpendicular to the stacking direction. The grid 104 removes unnecessary scattering radiation generated from an object 102 by arranging the lead plates aligned almost parallel to each other so that they match the direction in which the primary radiation is traveling.

If the grid 104 is a grid that has, for example, a specification of 52 lines per cm, the lead plate has a width of 40 μm and the aluminum plate has a width of 150 μm for a grid pitch of 190 μm. For example, in a grid that has a specification of 40 lines per cm, the lead plate has a width of 50 μm and the aluminum plate has a width 200 µm for a grid pitch of 250 µm. In practice, a grid ratio correlated with the radiation transmittance of the grid 104 is shown in the specification. Since the pixel pitch of each pixel of a radiation detection unit 105 has, for example, a range between 100 µm to 200 µ, the grid pitch of the grid 104 and the pixel pitch are very close. Therefore, if the position of the grid 104 is shifted just by a few µm, the output value (pixel value) of the automatic exposure control pixel 106 may greatly change.

Figure 5A:
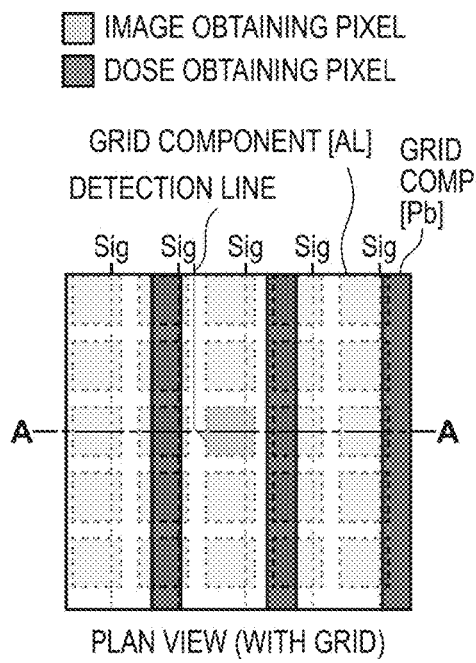

FIGS. 5A to 5F are views for explaining the arrangement of the radiation detection unit 105 of the radiation imaging apparatus according to the second embodiment. FIG. 5A is a plan view when there is the grid 104. The plan view of FIG. 5A is a view seen from the side of the grid 104, and the radiation detection unit 105 is arranged on the back side of the grid. In FIG. 5A, each grid component AL indicates a portion where the grid 104 is formed by an aluminum member and each grid component Pb indicates a portion where the grid 104 is formed by a lead member. In FIG. 5A, the grid components AL and the grid components Pb are arranged at a pitch close to the pixel arrangement pitch (pixel pitch) of the radiation detection unit 105.

Figure 5B:
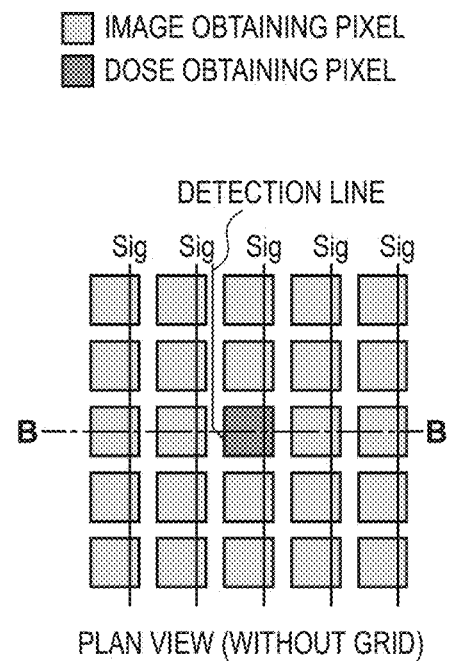

FIG. 5B is a plan view showing the example of pixel arrangement of the radiation detection unit 105 when there is no grid 104. Assume that, for FIG. 5A, the pixels of the radiation detection unit 105 are also arranged in the same manner as shown in FIG. 5B. The pixel arrangement of the radiation detection unit 105 includes image obtaining pixels to be used for a radiation image capturing operation and the automatic exposure control pixel 106 (dose obtaining pixel) for outputting an arrival dose before the image capturing operation. The pixels (image obtaining pixels and dose obtaining pixel) each are connected to a corresponding signal line (Sig line), and the corresponding signal line (Sig line) outputs the signal of each pixel. Other than the signal line (Sig line), a detection line is connected to the automatic exposure control pixel 106 (dose obtaining pixel). The automatic exposure control pixel 106 (dose obtaining pixel) outputs information (output signal) indicating the arrival radiation dose through the detection line under the control of a detection control unit 107.

Radiation 103 that reaches each image obtaining pixel is converted into an electric signal by a photoelectric conversion element. By driving a TFT or the like which is controlled by the detection control unit 107, the output signals output from the pixels (image obtaining pixels) via the corresponding signal lines (Sig lines) become a radiation image when the pixel values are rearranged in an image processing unit 114.

On the other hand, before being read out via the signal line (Sig line), the automatic exposure control pixel 106 (dose obtaining pixel) outputs the information indicating the arrival radiation dose via the detection line which is controlled by the detection control unit 107. The information indicating the output arrival radiation dose is calibrated by a calibration control unit 112 based on calibration data stored in a calibration data storage unit 111. The automatic exposure control pixel 106 performs real-time detection under the control of the detection control unit 107 and outputs a calibrated correct output value (output signal) to the detection control unit 107. The detection control unit 107 accumulates the output value (output signal). If the accumulated output value (output signal) is larger than a predetermined threshold which indicates that a predetermined dose has been reached, the detection control unit 107 outputs a radiation exposure termination signal to a radiation generating unit 101. Upon receiving the radiation exposure termination signal, the radiation generating unit 101 stops generating the radiation 103.

Figure 5C:
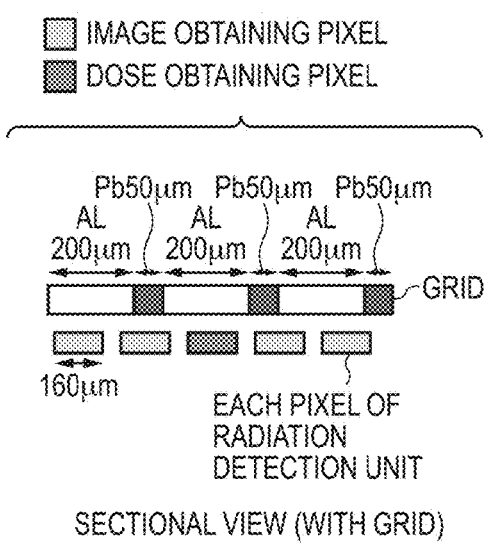
Figure 5D:
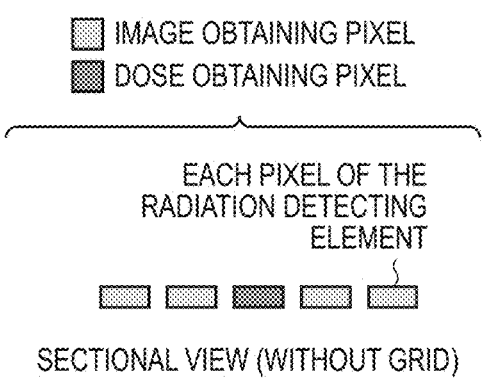

FIG. 5C is a view showing a section taken along a line A-A shown in FIG. 5A and exemplarily shows the sectional structure of the grid and the radiation detection unit. In FIG. 5C, each grid component AL has a width of 200 µm, each grid component Pb has a width of 50 µm, and the pixels (image obtaining pixels and dose obtaining pixel) each have a size of 160 µm. FIG. 5D is a view showing a section taken along a line B-B shown in FIG. 5B, and the size of the pixels each are 160 µm in the same manner as the pixels of FIG. 5C.

FIGS. 5E and 5F are views each showing, in association with the arrangement positions of the pixels and in a two-dimensional manner, the output values which are output from the image obtaining pixels used for radiation image capturing. In FIGS. 5E and 5F, since the output value of the dose obtaining pixel is not used for image obtainment, it is left blank. 25×25 image obtaining pixels are arranged around the dose obtaining pixel as the center. The arrangement of the image obtaining pixels is exemplary, and a calibration data generating unit 110 can select various image obtaining pixel arrangements for the generation of calibration data.

In the output example of the pixels without the grid (FIG. 5F), the output value of each pixel other than the dose obtaining pixel indicates "10" and the distribution of the output values is uniform. On the other hand, in the output example of the pixels with the grid (FIG. 5E), the output values of pixels, arranged around the dose obtaining pixel under the influence of the grid, vary just by being shifted by one pixel. For example, pixels indicating the output value "5" exist together with pixels indicating the output value "10", thus showing that pixels that indicate half the value of the output value also exist. Since the grid 104 may be moved in small increments with respect to the radiation detection unit 105, knowing the grid arrangement at the state of installation is important.

If the dose obtaining pixel is to be used for capturing a radiation image, a defective region may be generated due to a difference in the respective output values of the dose obtaining pixel and the surrounding pixels as in the above described example. On the other hand, if the output value of the dose obtaining pixel becomes equal with the output values of the surrounding pixels, the dose obtaining pixel can be used for image obtainment.

In order to function the dose obtaining pixel as the image obtaining pixels, the absolute value of the output value of the pixel needs to be calibrated. The output value of the dose obtaining pixel may change if the geometrical arrangement relationship of the grid 104 and the radiation detection unit 105 changes. According to the arrangement of the second embodiment, even when a radiation imaging operation is performed by a mobile X-ray car in which the geometrical arrangement relationship of the grid 104 can change with respect to the radiation detection unit 105 which has been reduced in weight, automatic exposure control can be executed by performing the following calibration data generation and calibration processing. The second embodiment will describe below the calibration method for appropriately calibrating the output value of the automatic exposure control pixel related to such a grid. The arrangement of the radiation imaging apparatus has the same arrangement as that described in FIG. 1. Processes of the second embodiment will be executed by the units of the arrangement in FIG. 1.

The calibration method of the automatic exposure control pixel 106 (dose obtaining pixel) when the grid 104 is used will be described in detail with reference to FIG. 4. First, in step S401, the geometric positional relationship of the grid 104 and the radiation detection unit 105 is changed. Next, in step S402, the radiation detection unit 105 obtains a radiation image for calibration data generation based on the output values of the image obtaining pixels. The radiation 103 from the radiation generating unit 101 is transmitted through the grid 104 and reaches the radiation detection unit 105, and an output signal is output from the automatic exposure control pixel 106 (dose obtaining pixel) when the radiation image is obtained by the radiation detection unit 105.

In step S403, when the radiation image for calibration data generation is obtained in the preceding step S402, the calibration data storage unit 111 stores the output signal of the automatic exposure control pixel 106 (dose obtaining pixel) that was transmitted through the grid 104. The calibration data storage unit 111 also stores the output signals of the image obtaining pixels that were transmitted through the grid 104. A first index generating unit 108 generates index information from the output signal of the dose obtaining pixel. The calibration data storage unit 111 stores the output signal output from the dose obtaining pixel and the index information generated by the first index generating unit 108.

In step S404, a second index generating unit 109 generates index information from the output signals of the image obtaining pixels. The image obtaining pixels are a plurality of pixels arranged around the dose obtaining pixel. The calibration data storage unit 111 stores the output signals output from the image obtaining pixels and the index information generated by the second index generating unit 109.

In step S405, the calibration data generating unit 110 compares the index information (first index information) generated by the first index generating unit 108 and the index information (second index information) generated by the second index generating unit 109 that were obtained in steps S403 and S404, respectively. Based on the result of the comparison, the calibration data generating unit 110 estimates the dose output of the dose obtaining pixel, generates calibration data so that the dose output of the dose obtaining pixel becomes equal to the outputs of the image obtaining pixels, and stores the generated calibration data in the calibration data storage unit 111.

In step S406, the calibration control unit 112 reflects the calibration data generated by the calibration data generating unit 110 on the output value of the automatic exposure control pixel 106 (dose obtaining pixel) and calibrates the output value of the dose obtaining pixel (calibration processing).

In step S407, the calibration data control unit 112 determines whether the respective output values (pixel characteristics) of the automatic exposure control pixel 106 (dose obtaining pixel) and the surrounding plurality of pixels (image obtaining pixels) including the grid 104 are equal. For example, if the difference of the output values (pixel characteristics) is larger than the predetermined threshold, the calibration control unit 112 determines that the output values (pixel characteristics) have changed (NO in step S407), and the process advances to step S408.

In step S408, a notification unit 113 displays a warning on a display unit 117 to notify the user of the change in the respective output values (pixel characteristics) of the dose obtaining pixel and the surrounding plurality of pixels (image obtaining pixels), and the process returns to step S402. Subsequently, the same processes are repeated from step S402.

On the other hand, if the difference of the output values (pixel characteristics) is equal to or more than the predetermined threshold in step S407, the calibration control unit 112 determines that the output values (pixel characteristics) are equal (YES in step S407), and the process advances to step S409. In step S409, the process changes to the next radiation imaging. By calibrating the dose obtaining pixel, radiation imaging can be performed, in the next radiation imaging operation, in a state in which the respective output values (pixel characteristics) of the dose obtaining pixel and the surrounding plurality of pixels (image obtaining pixels) have not changed.

According to the second embodiment, even when the scattering radiation removing grid is used, the output value of a dose grasping pixel can be calibrated by using the output signals of the image obtaining pixels.

(Third Embodiment)

Processing for a case in which there is a temporal change in an output value of each automatic exposure control pixel 106 (dose obtaining pixel) will be described in the third embodiment. The arrangement of a radiation imaging apparatus has the same arrangement as that described in FIG. 1. Processes of the third embodiment will be executed by the units of the arrangement in FIG. 1.

Figure 6:
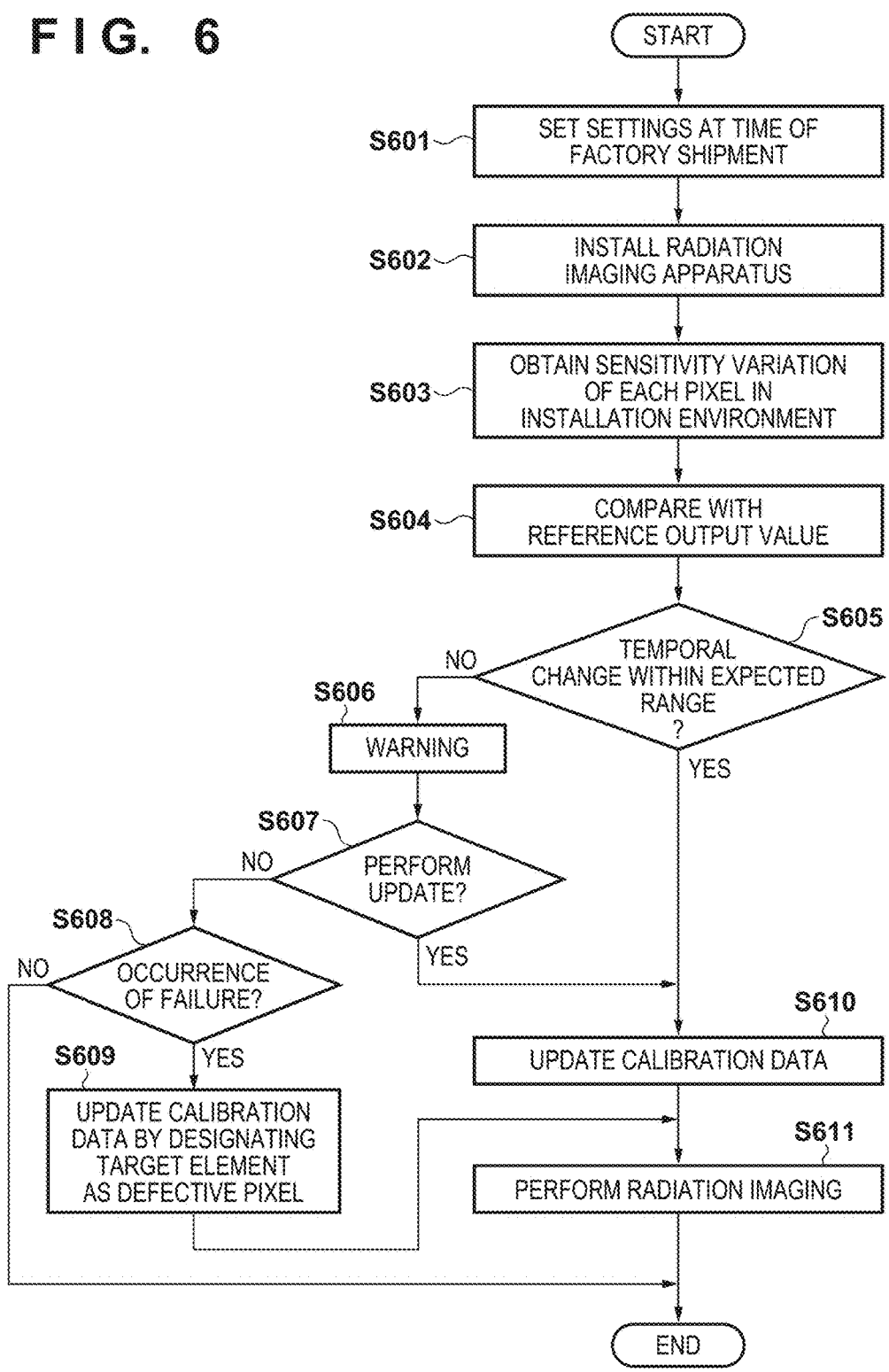
FIG. 6 is a flowchart for explaining the operation sequence of a radiation imaging apparatus according to the third embodiment.

FIG. 6 is a flowchart for explaining the operation sequence of the radiation imaging apparatus according to the third embodiment. In step S601, settings at the time of factory shipment are set for the radiation imaging apparatus. In step S602, the radiation imaging apparatus is installed. Next, in step S603, a detection control unit 107 of the radiation imaging apparatus obtains the sensitivity variation of pixels in the environment where the radiation imaging apparatus is installed. The detection control unit 107 can obtain the result of pixel sensitivity variation by, for example, a test image capturing operation performed by a serviceman or the like at the time of installing the radiation imaging apparatus.

In step S604, the detection control unit 107 compares the output value of the automatic exposure control pixel 106 (dose obtaining pixel) and a reference output value as a reference for determining the presence/absence of temporal change. Assume that the reference output value as the reference for determining the presence/absence of temporal change has the time of the installation of the radiation imaging apparatus as the starting point, and a plurality of reference output values corresponding to a time-series are stored, for example, in a calibration data storage unit 111. The detection control unit 107 selects the reference output value according to the time passed (for example, year, month, day, hour, and the like) from the time of installation, and the detection control unit 107 compares the selected reference output value and the output value of the automatic exposure control pixel 106 (dose obtaining pixel).

In step S605, based on the comparison result of the preceding step S604, if the output value of the dose obtaining pixel is equal to or larger than the reference output value (YES in step S605), the detection control unit 107 determines that the temporal change is within an expected range (within a predetermined range).

In step S610, a calibration data generating unit 110 updates the calibration data. The update information used for updating the calibration data has, for example, the time of the installation of the radiation imaging apparatus as the starting point, and a plurality of pieces of update information corresponding to a time series (for example, year, month, day) are stored in the calibration data storage unit 111. The calibration data generating unit 110 selects a corresponding piece of update information according to the time passed from the time of installation or the period of use of the radiation detection unit 105 and updates the calibration data. A calibration control unit 112 calibrates the output value of the automatic exposure control pixel 106 (dose obtaining pixel) based on the update information selected by the calibration data generating unit 110.

A radiation imaging operation is performed in step S611. The automatic exposure control pixel 106 (dose obtaining pixel) performs real-time detection under the control of the detection control unit 107 and outputs the calibrated correct output value (output signal) to the detection unit 107. If the accumulated output value (output signal) is larger than a predetermined threshold which indicates that a predetermined radiation dose has been reached, the detection control unit 107 outputs a radiation exposure termination signal to the radiation generating unit 101. The radiation generating unit 101 stops the generation of the radiation upon receiving the radiation exposure termination signal, so the radiation imaging operations ends.

On the other hand, in step S605, based on the comparison result of the preceding step S604, if the output value of the dose obtaining pixel becomes smaller than the reference output value, the detection control unit 107 determines that a temporal change which exceeds the expected range (predetermined range) has been generated. In step S606, a notification unit 113 displays a warning, based on the determination result of the detection control unit 107, on a display unit 117 to notify the user that the temporal change which exceeds the expected range has been generated.

In step S607, the notification unit 113 causes the display unit 117 to display a GUI requesting the user to determine whether to update the calibration data. If an operation input to perform the updating of calibration data is input via the GUI (YES in step S607), the process advances to step S610. In step S610, the calibration data update processing is performed by the same process as described above. In this case, the output value of the automatic exposure control pixel 106 (dose obtaining pixel) influenced by the temporal change exceeding the expected range is calibrated based on the updated calibration data.

On the other hand, in step S607, if an operation input not to perform the updating of calibration data is input via the GUI (NO in step S607), the process advances to step S608. A determination to check whether a failure has occurred is performed in step S608. The determination of whether a failure has occurred is, for example, determined by the detection control unit 107. The detection control unit 107 determines whether each pixel of the radiation unit 105 is operating normally by supplying a driving signal to a radiation detection unit 105 and monitoring the response signal of the radiation detection unit 105 for the driving signal. Alternatively, the user can check each unit of the radiation imaging apparatus to determine whether a failure has occurred.

In step S608, if no failure is determined (NO in step S608), the process ends. On the other hand, if a pixel that is not operating normally is determined to be present (failure) by the determination of step S608 (YES in step S608), the process advances to step S609.

In step S609, the calibration data generating unit 110 excludes the failure target pixel (target pixel) as a defective pixel from the image obtaining pixels and updates the calibration data without using the pixel value of the target pixel for calibrating the output value of the dose obtaining pixel. If a plurality of image obtaining pixels have been weighted, the calibration data generating unit 110 updates the calibration data by changing the settings of the weighting coefficient to zero or to a weighting coefficient that is smaller than the setting value of the current weighting coefficient to reduce the influence of the target pixel. The calibration control unit 112 calibrates the output value of the automatic exposure control pixel 106 (dose obtaining pixel) based the calibration data updated by the calibration data generating unit 110.

Subsequently, in step S610, the radiation imaging operation is performed. The automatic exposure control pixel 106 (dose obtaining pixel) performs real-time detection under the control of the detection control unit 107 and outputs the calibrated correct output value (output signal) to the detection unit 107. The detection control unit 107 accumulates the output value (output signal). If the accumulated output value (output signal) is larger than a predetermined threshold which indicates that a predetermined dose has been reached, the detection control unit 107 outputs the radiation exposure termination signal to the radiation generating unit 101. The radiation generating unit 101 stops the generation of the radiation upon receiving the radiation exposure termination signal, so the radiation imaging operations ends.

According to the arrangement of the third embodiment, in accordance with a case in which a temporal change has occurred in the output signal of the dose obtaining pixel or a case in which a failure has occurred in the image obtaining pixels, the calibration data is updated and the output value of the dose obtaining pixel can be calibrated based on the updated calibration data.

(Fourth Embodiment)

An arrangement for generating calibration data based on a distribution tendency of the output values of a plurality of dose obtaining pixels and a comparison with a past calibration result will be described in the fourth embodiment. FIG. 7 is a flowchart for explaining the operation sequence of a radiation imaging apparatus according to the fourth embodiment. The arrangement of the radiation imaging apparatus has the same arrangement as that described in FIG. 1. Processes of the fourth embodiment will be executed by the units of the arrangement in FIG. 1. In step S701, a radiation detection unit 105 obtains a radiation image. Radiation 103 from a radiation generating unit 101 reaches the radiation detection unit 105, and output signals are output from automatic exposure control pixels 106 (dose obtaining pixels) when the radiation image is obtained by the radiation detection unit 105.

In step S702, a detection control unit 107 obtains the output values (dose outputs) of the automatic exposure control pixels 106 (dose obtaining pixels), performs mapping processing to associate the values to the respective arrangement positions of the dose obtaining pixels, and generates information that two-dimensionally shows the distribution of the output values. A display unit 117 can display the result of the mapping processing. A user can grasp the distribution tendency of the output values (dose outputs) based on this display. The detection control unit 107 can also determine the tendency of the distribution. For example, (a) if the output values (dose outputs) of the dose obtaining pixels decrease overall in the same tendency and are equal to or smaller than a predetermined threshold (first threshold), the detection control unit 107 can determine that the distribution tendency is caused by a temporal factor; (b) if the output values (dose outputs) of the dose obtaining pixels partially decrease and the output values of some of the dose obtaining pixels are equal to or smaller than a predetermined threshold (second threshold), the detection control unit 107 can determine that the distribution tendency is caused by the grid arrangement; and (c) if the output values of the dose obtaining pixels decrease overall in the same tendency to be equal to or smaller than the first threshold and the output values of some of the dose obtaining pixels further decrease to be equal to or smaller than the second threshold, the detection control unit 107 determines that the distribution tendency is caused by a temporal factor and the grid arrangement.

In step S703, a calibration data generating unit 110 estimates the output values (dose outputs) of the dose obtaining pixels from the pixel values of the captured radiation image and generates the calibration data. In step S704, the calibration data generating unit 110 compares the generated calibration data with calibration data of a past calibration processing operation. If the temporal change of the generated calibration data is different from the calibration data of the past calibration processing operation, a change in the arrangement position of a scattering radiation removing grid, a temporal change of the automatic exposure pixels 106 (dose obtaining pixels), or the like can be raised as candidates of the cause of dose output change. For example, (a) if the change is caused by the influence of the temporal change of the dose obtaining pixels, the calibration data generating unit 110 can generate calibration data by the processing described in the third embodiment; (b) if the change is caused by the influence of the grid arrangement, the calibration data generating unit 110 can generate the calibration data by the processing described in the second embodiment; and (c) if the change is caused by the temporal factor and the grid arrangement, the calibration data generating unit 110 can generate the calibration data obtained by combining calibration data from the respective processes described in the second embodiment and the third embodiment.

In step S705, a calibration control unit 112 calibrates the output values of the dose obtaining pixels based on the calibration data generated in the preceding step S704. If the output values are changed to be larger than a predetermined threshold or if only the output value of a certain dose obtaining pixel is changed to be larger than the predetermined threshold, a notification unit 113 can display a warning on the display unit 117 to notify the user of such a change and display the past calibration data history.

In step S706, a user-administrator or a sales and service representative of the radiation imaging apparatus determines whether the output values (output signals) of the dose obtaining pixels which the calibration data are fine. If the imaging conditions for obtaining the radiation image are to be changed (NO in step S706), for example, as in a case in which the radiation image obtained for calibration was obtained under different conditions than the actual imaging operation, the process returns to step S701, and the processing is repeated in the same manner. On the other hand, if the determination in step S706 is "OK" (YES in step S706), the process advances to step S707.

In the radiation imaging operation of step S707, the automatic exposure pixels 106 (dose obtaining pixels) performs real-time detection under the control of the detection control unit 107 and outputs the calibrated correct output values (output signals) to the detection unit 107. The detection control unit 107 accumulates the output values (output signals). If the accumulated output values (output signals) are larger than a predetermined threshold which indicates that a predetermined dose has been reached, the detection control unit 107 outputs a radiation exposure termination signal to the radiation generating unit 101. The radiation generating unit 101 stops the generation of the radiation upon receiving the radiation exposure termination signal, so the radiation imaging operations ends.

(Fifth Embodiment)

Figure 8A:
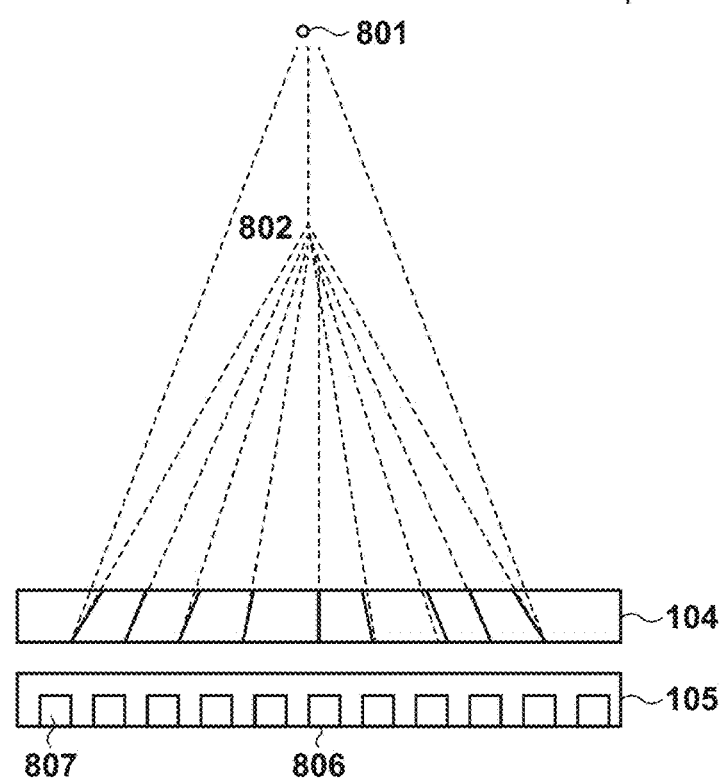
FIGS. 8A to 8C are views for explaining the sequence of calibration data generating processing of a radiation imaging apparatus according to the fifth embodiment.
Figure 8B:
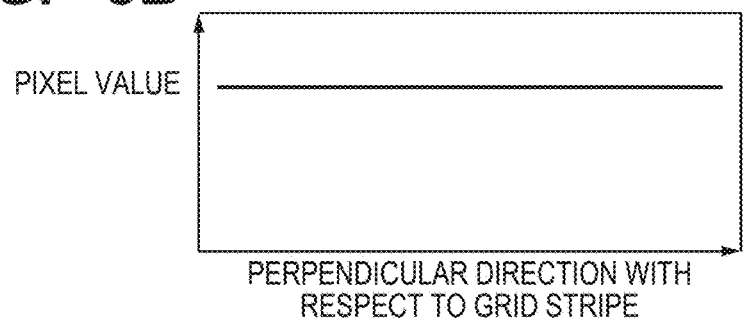
Figure 8C:
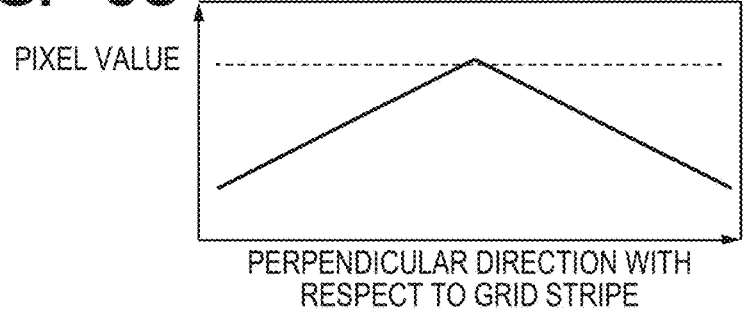

Processing for a case in which a focal distance of a radiation imaging unit 101 changes with respect to a grid will be described in the fifth embodiment. FIGS. 8A to 8C are views for explaining the sequence of calibration data generating processing of a radiation imaging apparatus according to the fifth embodiment. The arrangement of the radiation imaging apparatus has the same arrangement as that described in FIG. 1, and processes of the fifth embodiment will be executed by the units of the arrangement in FIG. 1.

FIG. 8A shows a state in which the radiation generating unit 101 is arranged at a first focal distance 801 and a state in which the radiation generating unit 101 is arranged at a second focal distance 802. Reference numerals 104 and 105 indicate a grid and a detection unit, respectively. When a radiation imaging operation that uses the grid 104 is performed, calibration data for calibrating an output value of each dose obtaining pixel changes if the position of the radiation generating unit 101 with respect to the grid changes. This is because the distribution of transmittance changes depending on whether the position of the radiation generating unit 101 matches with or changes from the focal distance of the scattering radiation removing grid 104. The distribution of transmittance of this grid is sometimes referred to as grid cutoff.

If a distribution profile of pixel values in a perpendicular direction to the grid stripes of the radiation image is obtained in the radiation image obtained by the radiation detection unit 105, for example, the distribution profiles as shown in FIGS. 8B and 8C can be obtained.

FIG. 8B is graph showing the relationship of the pixel values when the position of the radiation generating unit 101 and the focal position with respect to the grid 104 match and the positions of the pixel values in the perpendicular direction to the grid stripes of the radiation image. The relationship shown in FIG. 8B corresponds to a state in which the radiation generating unit 101 is arranged at the first focal distance 801.

FIG. 8C is a graph showing the relationship of the pixel values when the position of the radiation generating unit 101 and the focal position with respect to the grid 104 do not match and the positions of the pixel values in the perpendicular direction to the grid stripes of the radiation image. The relationship shown in FIG. 8C corresponds to a state in which the radiation generating unit 101 is arranged at the second focal distance 802. The broken lines shown in FIG. 8C are lines that indicate the distribution of pixel values of FIG. 8B for comparison.

An ideal distribution profile of pixel values is a profile in which the distribution of pixel values is uniform as shown in FIG. 8B. However, if the position of the radiation generating unit 101 differs from the focal position with respect to the grid 104, the distribution of the pixel values becomes non-uniform as shown in FIG. 8C. That is, the incident radiation dose to a dose obtaining pixel 806 positioned at the center of the grid 104 is not affected by the difference in the focal position. However, as the position of the radiation generating unit 101 becomes close to the sides of the end portions (in the left and right directions of the page) of the grid 104, the incident radiation dose, that is the arrival radiation dose, to a dose obtaining pixel 807 arranged at the end portion of the radiation detection unit 105 is reduced by the difference in the focal position. Therefore, in order to calibrate the grid cutoff, the influence of the distance (focal distance) between the radiation generating unit 101 and the grid 104 need to be considered in addition to each dose obtaining pixel and each output value of the dose obtaining pixel. That is, by considering the positional relationship of the arrangement of the grid 104 and the radiation detection unit 105 and the relationship of the distance (focal distance) between the radiation generating unit 101 and the grid 104 for the generation of calibration data, calibration data with reduced influence of the grid cutoff can be generated.

For example, as shown in FIG. 8C, if the position of the radiation generating unit 101 and the focal position with respect to the grid 104 do not match, a detection control unit 107 determines the distribution tendency of known arrival doses by using the statistical value or the average value of the pixels surrounding each dose obtaining pixel. If the distribution tendency of the arrival dose becomes, for example, like the distribution tendency shown in FIG. 8B, the detection control unit 107 determines that the position of the radiation generating unit 101 and the focal position with respect to the grid 104 match. If the distribution tendency of the arrival dose becomes, for example, like the distribution tendency shown in FIG. 8C, the detection control unit 107 determines that the position of the radiation generating unit 101 and the focal position of the grid 104 do not match. A notification unit 113 causes a display unit 117 to display a warning, based on the determination result of the detection control unit 107, to notify a user that an error will be generated in the output value (output signal) output from the dose obtaining signal depending on the selection of the dose obtaining pixel to be used. In the fifth embodiment, the same determination is performed for the grid cutoff when the focal position moves in a direction perpendicular to the grid stripes.

A calibration data generating unit 110 generates calibration data for calibrating the distribution profile of FIG. 8C to the distribution profile of FIG. 8B. For example, in FIG. 8C, the incident radiation dose to the dose obtaining pixel 806 corresponding to a position (center of the grid) on the optical axis between the radiation generating unit 101 and the grid 104 is not affected by a difference in the focal position. When imaging is performed using the grid, the detection control unit 107 determines the distribution tendency of the output values output from the image obtaining pixels arranged around each dose obtaining pixel. If the distribution of the output values is non-uniform, the calibration data generating unit 110 generates the calibration data so that the distribution tendency of the output values becomes uniform by using, as a reference, the output value of the dose obtaining pixel corresponding to the position (center of the grid) on the optical axis between the radiation generating unit 101 and the grid 104. Based on the calibration data generated by the calibration data generating unit 110, a calibration control unit 112 calibrates the output value of each dose obtaining pixel. The generation of calibration data when using the grid 104 is the same as that described in the second embodiment. Based on the calibration data, the calibration control unit 112 calibrates the change of the output value of each dose obtaining pixel that corresponds to the change in the focal distance between the radiation generating unit 101 and the grid 104 and the change in the relative position between the grid 104 and the radiation detection unit 105.

According to the fifth embodiment, each dose obtaining pixel can be calibrated by generating calibration data in consideration of the positional relationship between the arrangement of the grid 104 and the radiation detection unit 105 and the relationship of the distance (focal distance) between the radiation generating unit 101 and the scattering radiation removing grid 104.

According to the embodiments described above, each dose grasping pixel can be calibrated by using the respective output values of the dose grasping pixel and the image obtaining pixels in accordance with the state of usage of the radiation imaging apparatus.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-261246, filed Dec. 24, 2014, which is hereby incorporated by reference herein in its entirety.

What is claimed is:

1. A radiation imaging apparatus comprising:
   a radiation detection unit including an image obtaining pixel for obtaining a radiation image and a dose obtaining pixel for obtaining a radiation dose;
   a calibration data generating unit configured to compare information obtained from an output value of the image obtaining pixel and information obtained from an output value of the dose obtaining pixel, and generate calibration data for calibrating an output value of the dose obtaining pixel so that the information based on the output value of the image obtaining pixel and the information based on the output value of the dose obtaining pixel become equal; and
   a calibration control unit configured to calibrate the output value of the dose obtaining pixel by using the calibration data.

2. The apparatus according to claim 1, wherein the calibration data generating unit generates the calibration data for calibrating the output value of the dose obtaining pixel by comparing index information obtained by statistical processing of the output value of the image obtaining pixel and index information obtained by statistical processing of the output value of the dose obtaining pixel.

3. The apparatus according to claim 1, wherein the calibration data generating unit compares index information based on the output value of the image obtaining pixel corresponding to radiation transmitted through a grid and index information based on the output value of the dose obtaining pixel corresponding to radiation transmitted through the grid, and
the calibration data generating unit generates the calibration data so that the index information based on the output value of the image obtaining pixel and the index information based on the output value of the dose obtaining pixel become equal.

4. The apparatus according to claim 3, wherein the calibration control unit calibrates, based on the calibration data, a change in the output value of the dose obtaining pixel corresponding to a change in a relative position between the grid and the radiation detection unit.

5. The apparatus according to claim 1, wherein the calibration data generating unit compares a reference output value for determining whether a temporal change of the dose obtaining pixel is within a predetermined range and the output value of the dose obtaining pixel, and
the calibration data generating unit updates, when the temporal change is within the predetermined range in the comparison result, the calibration data by update information corresponding to a period of use of the radiation detection unit.

6. The apparatus according to claim 5, further comprising a notification unit configured to notify, when the temporal change of the dose obtaining pixel exceeds the predetermined range in the comparison result, generation of the temporal change that exceeds the predetermined range.

7. The apparatus according to claim 6, wherein the calibration data generating unit updates, when the generation of the temporal change is notified, the calibration data by the update information corresponding to the period of use of the radiation detection unit based on an operation input.

8. The apparatus according to claim 1, further comprising:
a detection control unit configured to control an operation of the radiation detection unit, wherein
the detection control unit determines whether each pixel of the radiation detection unit is operating normally by a response signal of the radiation detection unit to a driving signal input by the radiation detection unit.

9. The apparatus according to claim 8, wherein the calibration data generating unit generates, when the detection control unit determines that there is a pixel not operating normally in the radiation detection unit, the calibration data by excluding the pixel not operating normally.

10. The apparatus according to claim 8, wherein the detection control unit outputs, when an accumulated value of the output value of the calibrated dose obtaining pixel reaches a predetermined radiation dose, a radiation exposure termination signal to a radiation generating unit which generates the radiation, and
the radiation generating unit stops generating the radiation by the radiation exposure termination signal.

11. The apparatus according to claim 8, wherein the detection control unit comprises a unit configured to generate information indicating an output value distribution that associates respective output values of a plurality of dose obtaining pixels with respective arrangement positions of the dose obtaining pixels, and a unit configured to determine a tendency of the output value distribution by comparing the information indicating the output value distribution and a threshold, and
the calibration data generating unit generates, when the generated calibration data differs from calibration data of past calibration processing, calibration data corresponding to the tendency of the determined distribution.

12. The apparatus according to claim 8, wherein the detection control unit determines, when a grid is used to perform imaging, an output value distribution of the image obtaining pixel arranged around the dose obtaining pixel, and
the calibration data generating unit generates, when the output value distribution is non-uniform, calibration data so that the output value distribution becomes uniform by using, as a reference, an output value of a dose obtaining pixel corresponding to a position on an optical axis between a radiation generating unit and the grid.

13. The apparatus according to claim 12, wherein the calibration control unit calibrates, based on the calibration data, a change in the output value of the dose obtaining pixel that corresponds to a change in a focal distance between the radiation generating unit and the grid and a change in a relative position between the grid and the radiation detecting unit.

14. The apparatus according to claim 1, wherein the radiation detection unit is a two-dimensional radiation sensor in which the image obtaining pixel and the dose obtaining pixel are arranged two-dimensionally, and
the image obtaining pixel comprises a plurality of image obtaining pixels arranged around the dose obtaining pixel.

15. An imaging control apparatus that controls a radiation detection unit including an image obtaining pixel for obtaining a radiation image and a dose obtaining pixel for obtaining a radiation dose, comprising:
a calibration data generating unit configured to compare information obtained from an output value of the image obtaining pixel and information obtained from an output value of the dose obtaining pixel, and generate calibration data for calibrating an output value of the dose obtaining pixel so that the information based on the output value of the image obtaining pixel and the information based on the output value of the dose obtaining pixel become equal; and
a calibration control unit configured to calibrate the output value of the dose obtaining pixel by using the calibration data.

16. An imaging control method of a radiation imaging apparatus comprising:
detecting radiation by using a radiation detection unit including an image obtaining pixel for obtaining a radiation image and a dose obtaining pixel for obtaining a radiation dose;
comparing information obtained from an output value of the image obtaining pixel and information obtained from an output value of the dose obtaining pixel, and generating calibration data for calibrating an output value of the dose obtaining pixel so that the information based on the output value of the image obtaining pixel and the information based on the output value of the dose obtaining pixel become equal; and calibrating the output value of the dose obtaining pixel by using the calibration data.

17. A non-transitory computer-readable storage medium storing a program for causing a computer to function as each unit of a radiation imaging apparatus, the radiation imaging apparatus comprising:
   a radiation detection unit including an image obtaining pixel for obtaining a radiation image and a dose obtaining pixel for obtaining a radiation dose;
   a calibration data generating unit configured to compare information obtained from an output value of the image obtaining pixel and information obtained from an output value of the dose obtaining pixel, and generate calibration data for calibrating an output value of the dose obtaining pixel so that the information based on the output value of the image obtaining pixel and the information based on the output value of the dose obtaining pixel become equal; and
   a calibration control unit configured to calibrate the output value of the dose obtaining pixel by using the calibration data.

18. A non-transitory computer-readable storage medium storing a program for causing a computer to function as each unit of an imaging control apparatus that controls a radiation detection unit including an image obtaining pixel for obtaining a radiation image and a dose obtaining pixel for obtaining a radiation dose, the imaging control apparatus comprising:
   a calibration data generating unit configured to compare information obtained from an output value of the image obtaining pixel and information obtained from an output value of the dose obtaining pixel, and generate calibration data for calibrating an output value of the dose obtaining pixel so that the information based on the output value of the image obtaining pixel and the information based on the output value of the dose obtaining pixel become equal; and
   a calibration control unit configured to calibrate the output value of the dose obtaining pixel by using the calibration data.

* * * * *